United States Patent
Nelson et al.

(10) Patent No.: US 7,127,299 B2
(45) Date of Patent: Oct. 24, 2006

(54) NETWORK COMMUNICATIONS ARRANGEMENT FOR IMD PROGRAMMING UNITS

(75) Inventors: Chester G. Nelson, Plymouth, MN (US); Charles Stomberg, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 441 days.

(21) Appl. No.: 10/035,462

(22) Filed: Oct. 23, 2001

(65) Prior Publication Data

US 2003/0078631 A1 Apr. 24, 2003

(51) Int. Cl.
*A61N 1/00* (2006.01)

(52) U.S. Cl. .......................................... 607/60; 607/31

(58) Field of Classification Search ............ 607/30–32, 607/60; 128/903–904; 604/891.1
See application file for complete search history.

(56) References Cited

U.S. PATENT DOCUMENTS

| | | | |
|---|---|---|---|
| 5,291,399 A | 3/1994 | Chaco | |
| 5,481,738 A | 1/1996 | Bartow et al. | |
| 5,497,460 A | 3/1996 | Bailey et al. | |
| 5,623,600 A * | 4/1997 | Ji et al. | 713/201 |
| 5,699,244 A | 12/1997 | Clark, Jr. et al. | |
| 5,752,917 A | 5/1998 | Fuchs | |
| 5,752,976 A | 5/1998 | Duffin et al. | |
| 5,790,953 A | 8/1998 | Wang et al. | |
| 6,249,705 B1 * | 6/2001 | Snell | 607/59 |
| 6,332,163 B1 * | 12/2001 | Bowman-Amuah | 709/231 |
| 6,386,882 B1 * | 5/2002 | Linberg | 434/262 |
| 6,574,503 B1 * | 6/2003 | Ferek-Petric | 600/523 |
| 6,622,050 B1 * | 9/2003 | Thompson | 607/60 |
| 6,650,944 B1 * | 11/2003 | Goedeke et al. | 607/60 |

* cited by examiner

*Primary Examiner*—Mark Bockelman
(74) *Attorney, Agent, or Firm*—Michael C. Soldner; Girma Wolde-Michael

(57) ABSTRACT

A medical data processing system that enables individual implanted medical device (IMD) programming units to securely access information networks that are susceptible to carrying data contaminants. In an example embodiment, a computer-implemented method for exchanging data with a plurality of implanted medical device (IMD) programming units, via a server arrangement that is coupled to a network, includes the step of establishing communication connections between the server arrangement and the plurality of IMD programming units. In response to receiving data at the server arrangement and destined for the IMD programming units, further including the step of identifying data contaminants in the received data and intercepting data containing data contaminants before the data reach the IMD programming units.

10 Claims, 1 Drawing Sheet

NETWORK COMMUNICATIONS ARRANGEMENT FOR IMD PROGRAMMING UNITS

FIELD OF THE INVENTION

The present invention generally relates to programming units used in connection with implantable medical devices. Specifically, the invention relates to a system and an arrangement for enabling an implant programming unit to interface with a data processing unit without receiving corrupted data or data contaminants.

BACKGROUND OF THE INVENTION

Implanted medical devices typically communicate via telemetry with an external implant programming unit using radio frequency signals. The programming unit downloads data to and receives data from the implanted medical device using a programmer head that extends from the programming unit. The programmer head includes an antenna that can be positioned over the patient's implanted device site for programming or telemetry interrogation of the implanted device.

Implant programming units are typically located in various locations in a medical facility and may be coupled to a local network or a public network. Access to printers or other peripherals is via direct (parallel or serial) connection. Most implant programming units include high-level processing capabilities and various software applications that facilitate many programming operations and local processing of data. Implant programming units require regular software upgrades that must be performed at each programming unit location. With technology evolving so quickly, medical facilities will also need to incur high capital investment costs in upgrading expensive programming units every few years.

In consulting with a patient having an implanted device, the physician may need to refer to literature, data, or an expert available on a medical information network or on the Internet, which may be necessary for diagnosis or instructing the patient. If the required information is not available during the exam, the physician may need to either call the patient later with the desired information or reschedule the exam. Providing implant programming units direct access to local networks or public networks, such as the Internet, can lead to inadvertent disclosure of confidential patient data that may be stored in the implant programming unit. A firewall (i.e., a combination of hardware and software that limits the exposure of a data processing unit from unauthorized access) is usually installed on the medical facility network or on individual desktop computers, but is not always effective at preventing infection from viruses or penetration by hackers.

There is a need for a system and an arrangement for enabling implant programming units to retrieve information that enhances the physician/patient visit without making the implant programming units accessible via local or public networks.

A system and an arrangement that addresses the aforementioned problems, as well as other related problems, are therefore desirable.

SUMMARY OF THE INVENTION

Various embodiments of the present invention are directed to addressing the above as well as other needs in connection with providing implant programming units having confidential information with protected access via a gateway server to information networks susceptible to carrying data contaminants. The gateway server not only blocks data contaminants but also blocks unauthorized access to the implanted programming units made via the information networks. Furthermore, the gateway server facilitates upgrades to a medical data processing system by providing a single point of access. In one example embodiment, the gateway server enables a user to access an implant programming unit for collaboration with another an implant programming unit. The user can also retrieve, print, format or export information via a network from the implant programming unit.

According to one embodiment of the invention, a computer-implemented method for exchanging data with a plurality of implanted medical device (IMD) programming units, via a server arrangement that is coupled to a network, includes the step of establishing communication connections between the server arrangement and the plurality of IMD programming units. In response to receiving data at the server arrangement that is destined for the IMD programming units, any data contaminants in the received data are identified and intercepted before the data reaches the IMD programming units.

According to another embodiment of the invention, a system is provided for programming implanted medical devices (IMDs). This system includes a plurality of IMD programming units, each programming unit facilitating sending data to, and retrieving data from, an IMD. A server arrangement, communicatively coupled to the plurality of IMD programming units, provides an interface between the programming units and a network. The server arrangement also receives the data via the network that is destined for the IMD programming units so that data contaminants may be identified and intercepted before the data reaches the IMD programming units.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawing, in which.

Figure 1:
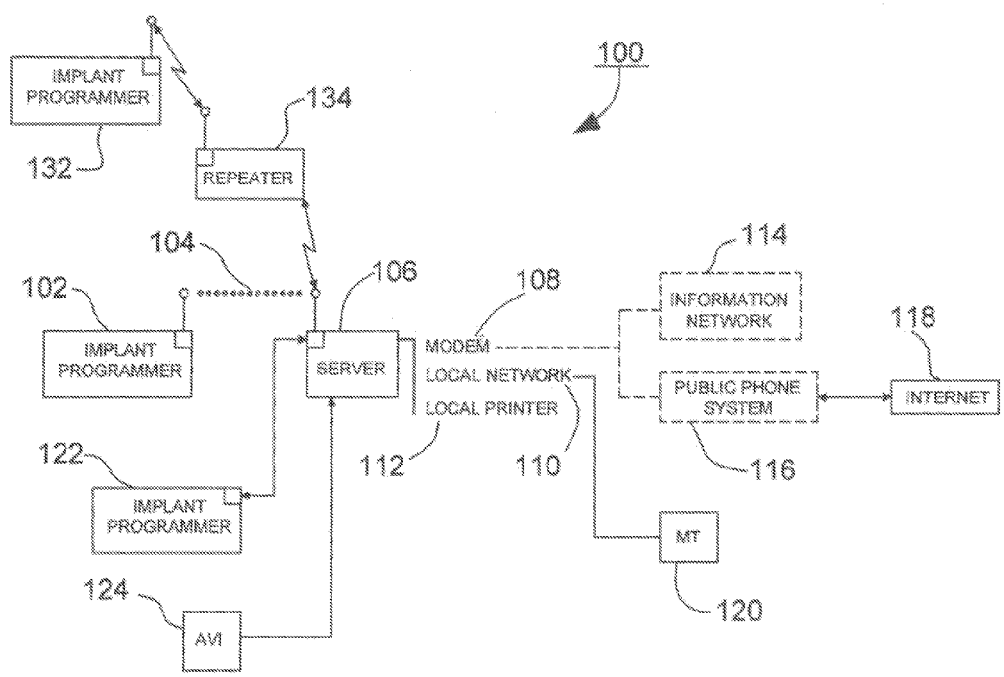
FIG. 1 is a block diagram of a medical data processing system that securely accesses data from an information network susceptible to carrying data contaminants according to an example embodiment of the invention.

While the invention is amenable to various modifications and alternative forms, specifics thereof have been shown by way of example in the drawing and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is directed to a medical data processing system that enables individual implanted device programming units to securely access information networks that are susceptible to carrying data contaminants. While the present invention is not necessarily limited to such an application, the invention will be better appreciated using a discussion of example embodiments in such a specific context.

In an example embodiment, implanted medical device (IMD) programming units that program and interrogate implanted medical devices have protected access, via a server arrangement shown as gateway server, to external networks that are susceptible to carrying data contaminants. The gateway server not only blocks data contaminants from reaching the IMD programming units but also blocks unauthorized access to confidential information residing on the IMD programming units. Data contaminants include, but are not limited to, viruses, worms, Trojan horses, macro viruses, MBR viruses or any other elements that corrupt data or disrupt data processing systems.

In a related embodiment, the confidential data normally stored on an individual IMD programming unit is stored at the gateway server. In addition, the gateway server includes the software applications that the implanted programming unit needs to program and interrogate an implanted device. The gateway server retrieves from network resources software applications, product information or data that is not immediately available on the server. The gateway server also communicates with the IMD programming units over the various communications paths or channels that include, but are not limited to, radio frequency channels, fiber optic channels, wireless communications channels using repeaters, and hardwire connections.

FIG. 1 is a block diagram of medical data processing system 100 that enables an implant programming unit to securely access data from an information network that is susceptible to carrying data contaminants, according to an example embodiment of the invention. Medical data processing system 100 includes a plurality of implant programming units 102, 122 and 132 that program and interrogate implanted medical devices. Patients with implanted devices are usually examined by physicians in rooms having one of the implant programming units.

Upon initializing programming unit 102, unit 102 establishes a radio frequency communications link 104 with a gateway server 106. Gateway server 106 provides firewall protection to units 102, 122 and 132 to prevent unauthorized access and to prevent the penetration of data contaminants. Gateway server 106 also provides access to a local network 110 and to a public network, such as the Internet 118. Once link 104 is established, implant programming unit 102 performs a self-discovery procedure in conjunction with gateway server 106. With the self-discovery procedure, programming unit 102 determines whether to continue initializing in its current mode or to reconfigure itself into a different mode based on software applications residing on gateway server 106. Once programming unit 102 is fully initialized, the physician is free to use programming unit 102 for programming and interrogating an implanted medical device of a patient. Through gateway server 106, programming unit 102 has access to outside networks via a modem 108 or access to a medical facility's local area network (LAN) 110. In addition, gateway server 106 reduces capital costs for the medical facility because programming units 102, 122 and 132 all have access to a local printer 112 and do not require standalone printers.

Gateway server 106 also facilitates protected access to external networks because server 106 includes hardware and software that provide firewall protection. The firewall is configured to block corrupted data that may be propagated along an external network. In addition, since the implant programming units contain confidential patient data, gateway server 106 includes software and hardware to prevent unauthorized access to the programming units. Physicians can, for example, use the implant programming unit to access the Harvard Medical School information network while consulting with a patient on the condition of the implanted medical device. Gateway server 106 blocks any corrupted data received via the external, network and verifies that the request for information is authorized before relaying the information to the proper implant programming unit.

Communications between implant programming unit 102 and gateway server 106 may be performed using TCP/IP protocol over a wireless (e.g., radio frequency signals) connection. For added security, information transferred between unit 102 and gateway server 106 is encrypted to provide a secure channel of communication. Communications between gateway server 106 and information network 114 and a public telephone system 116 are normally unsecured.

System 100 also includes an administrative user interface (AUI) unit 124 used for configuring gateway server 106 and the implant programming units. For instance, AUI 124 determines the level of access that users of implant programming units have when interfacing with gateway server 106. In another application, AUI 124 configures system 100 such that data collected at the various implant programming units will be stored exclusively at gateway server 106 and not at the respective programming units.

Gateway server 106 includes dynamic host Internet Protocol (IP) address assignment capability. This approach enables gateway server 106 to identify, and direct data to, each implant programming unit in the system. Gateway server 106 and programming unit 102 may communicate via the Simple Object Access Protocol (SOAP), which provides a mechanism that allows applications to communicate with each other over the Internet independent of the type of platform being utilized. Alternatively, the Extensible Markup Language (XML) protocol may be used to communicate data between the gateway server and the programming unit.

In a related embodiment, gateway server 106 manages various communication paths. In one application, implant programming unit 122 is directly hardwired to gateway server 106, and implant programming unit 132 communicates with server 106 via a wireless arrangement such as repeater 134. Units 102 and 132 provide mobility because they are free of hardware connections to the hospital or clinic network. For example, implant programming units 102 and 132 are movable from a physician's office to the operating room without disrupting the connection to the network. Wireless range for the programming units depends on the type of wireless technology and system selected. In one application, the wireless range is about 100–150 feet. In this example, the wireless technology is consistent with IEEE standard 802.1 lb.

Wireless connection 104 from unit 102 to gateway server 106 provides electrical isolation between implant programming unit 102 and the external network, LAN or any locally attached peripheral. Because unit 102 and gateway server 106 are separate units, any malfunction at gateway server 106 does not impact unit 102. In one example, the lack of a physical electrical connection between implant programming unit 102 and gateway server 106 alleviates the need to electrically isolate an ECG monitored patient.

In one example application, the high bandwidth connection between gateway server 106 and programming unit 102 enables information transfer rates of about 5 Megabits/sec. With gateway server 106, programming unit 102 is kept continuously up-to-date because information (e.g., e-mails, reports, manual updates etc. . . . ) directed to programming unit 102 resides in storage device 103 on gateway server 106 and is available for immediate access. In this example, hardware and software sharing between gateway server 106 and programming unit 102 enables each device to mutually view and traverse each other's directories. However, gateway server 106 is not free to manipulate any resource on unit 102 because of sensitive functionality of the implant programming units.

Gateway server 106 provides a repository for additional information, information links and additional services that can be made available to users that have access to the gateway server. Clinics can share with other clinics programming preferences, phone books, reports, report formats and the like. Rules of engagement (types of reports, communication protocol used, encryption requirements, etc. . . . ) of various clinics are also displayed and are adopted by gateway server 106 when communicating with a certain clinic to increase speed and protect confidentiality of transferred data. In this embodiment, gateway server 106 can establish a communication connection with a plurality of communications protocols, thereby facilitating communication with various implant programming units located at various clinics. In a related embodiment, gateway server 106 securely archives patient session data (data obtained during a programming/interrogating session) within or outside of the gateway server. In another related embodiment, system 100 includes a master transmitter 120 located on LAN 110 that couples gateway server 106 to other external networks.

In still another related embodiment, gateway server 106 is configured as a "fat" device such that most of the processing power, memory, and application software and firmware used in system 100 reside on the gateway server while the implant programming units are the "thin" devices that are used as terminals that access the functionality from gateway server 106. For example, most of the application software running on the programming units could be stored in storage device 103. With this approach, the "thin" implant programming units are less expensive than a "fat" programming unit and more units can be added to system 100 without greatly increasing the cost to the medical facility of system 100. In this example, AUI 124 configures system 100 to recognize new implant programming units that are added to system 100. This approach greatly simplifies system upgrades and alleviates concerns of equipment obsolescence because the system upgrade is performed primarily at gateway server 106. System maintenance costs for the medical facility are also lower because copies of new software versions are not necessary for each implant programming unit.

According to another aspect of the invention, physician mobility may be enhanced with an implant programming unit that is comprised of a portable handheld computer in combination with a programming head attachment. The combination operates as a wireless implant programming unit that is communicatively coupled to gateway server 106.

Using the current invention, an implant programming unit can browse the Internet without loading the web browsing software directly on the implant programming unit. In the various embodiments, implant programming unit user preferences can reside on the gateway server and are quickly accessed when a user logs into system 100 at any implant programming unit. User preferences include the format in which the data is presented, font and spacing of written documents, order of reports, format of graphs and the like. In the various embodiments, data that is gathered by an implant programming unit can be customized as per a request by a user at the gateway server level. Additionally, the gateway server can facilitate collaboration by two implant programming units that are not co-located.

In an application wherein gateway server 106 is not engaged in system 100 (i.e., gateway server is down), the implant programming units can be connected directly to external networks via modem 108 or LAN 110. However, extreme caution must be taken to provide the implant programming unit with firewall software/hardware protection from data contaminants. In this example, the implant programming unit should have only limited access to external networks.

Networks that the gateway server can communicate with include a public telephone network, LAN, a WAN, internal public exchange, wireless, microwave, global satellite communications and the World Wide Web. For a more detailed discussion of the methods of communicating remotely with an IMD, reference may be made to U.S. Pat. No. 5,752,976 to Duffin et al, which is assigned to the assignee of the present invention and is incorporated herein by reference.

The present invention encompasses implant programming units that program and interrogate implanted medical devices that include, but are not limited to, cardiac defibrillators, pacemakers, drug pumps, neurological implants, nerve stimulators, various cardiac implants and equivalent medical devices. In addition, embodiments described are compatible with remote patient management systems that interact with remote data and expert data centers and also with a data communication system that enables the transfer of clinical data from the patient to a remote location for evaluation, analysis, data reposition, and clinical evaluation.

Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A system for programming implanted medical devices (IMDs), comprising:
 a data network;
 a gateway server arrangement coupled to the data network;
 an IMD programming unit to send data to, and retrieve data from, an IMD, the programming unit being coupled to the gateway server arrangement and comprising means for performing a self-discovery procedure to determine whether to initialize in a current mode or to reconfigure into a different mode that is based on software applications residing on the gateway server arrangement;
 wherein the server arrangement includes a network interface intercepting data contaminants included in data received via the network and destined for the IMD programming unit and includes a storage device wherein a portion of programmable instructions executed by the IMD programming unit are stored.

2. The system of claim 1, wherein the IMD programming unit and the server arrangement are further configured to exchange encrypted data.

3. The system of claim 1, wherein the server arrangement includes a radio signal transceiver coupled to the IMD programming unit.

4. The system of claim 3, wherein the server arrangement is coupled to the IMD programming unit by an electrically conductive wire.

5. The system of claim 4, wherein the server arrangement is coupled to the IMD programming unit by an optical fiber.

6. The system of claim 1, wherein the server arrangement is further configured to address the IMD programming unit using dynamic host Internet Protocol (IP) address assignments.

7. The system of claim 1, wherein the server arrangement is further configured to deny unauthorized access to the IMD programming unit that is attempted over the network.

8. The system of claim 1, wherein the server arrangement is coupled to multiple IMD programming units.

9. The system of claim 1, wherein the server arrangement is coupled to an administrative user interface provided to configure at least one of the server arrangement and the IMD programming unit.

10. The system of claim 1, wherein the server arrangement includes a storage device, and
 wherein at least some of the data received via the network and destined for the IMD programming unit is stored in the storage device.

* * * * *